(12) United States Patent
Xu et al.

(10) Patent No.: US 12,383,684 B2
(45) Date of Patent: Aug. 12, 2025

(54) AIRWAY ANOMALY RECOGNITION METHOD, VENTILATION DEVICE, AND STORAGE MEDIUM

(71) Applicants: SHENZHEN MINDRAY BIO-MEDICAL ELECTRONICS CO., LTD., Shenzhen (CN); Peking Union Medical College Hospital, Chinese Academy of Medical Science and Peking Union Medical C, Beijing (CN)

(72) Inventors: Jun Xu, Beijing (CN); Jinglei Liu, Shenzhen (CN); Xuezhong Yu, Beijing (CN); Yangyang Fu, Beijing (CN); Xinru Zou, Shenzhen (CN); Xiaoyong Zhou, Shenzhen (CN)

(73) Assignees: SHENZHEN MINDRAY BIO-MEDICAL ELECTRONICS CO., LTD., Shenzhen (CN); PEKING UNION MEDICAL COLLEGE HOSPITAL, CHINESE ACADEMY OF MEDICAL SCIENCE AND PEKING UNION MEDICAL COLLEGE, Beijing (CN)

( * ) Notice: Subject to any disclaimer, the term of this patent is extended or adjusted under 35 U.S.C. 154(b) by 987 days.

(21) Appl. No.: 17/159,142

(22) Filed: Jan. 26, 2021

(65) Prior Publication Data

US 2021/0213217 A1 Jul. 15, 2021

Related U.S. Application Data

(63) Continuation of application No. PCT/CN2018/101595, filed on Aug. 21, 2018.

(51) Int. Cl.
*A61M 16/00* (2006.01)

(52) U.S. Cl.
CPC ...... *A61M 16/0051* (2013.01); *A61M 16/022* (2017.08); *A61M 2016/0027* (2013.01);
(Continued)

(58) Field of Classification Search
CPC ............ A61M 16/0051; A61M 16/022; A61M 2016/0027; A61M 2016/003;
(Continued)

(56) References Cited

U.S. PATENT DOCUMENTS 5,540,220 A * 7/1996 Gropper ............ A61M 16/0051
128/204.26
5,743,253 A * 4/1998 Castor .................... G05B 17/02
128/204.23
(Continued)

FOREIGN PATENT DOCUMENTS

AU 2011356176 A1 7/2013
CN 102441209 A 5/2012
(Continued)

OTHER PUBLICATIONS

International Search Report issued in corresponding International Application No. PCT/CN2018/101595, mailed May 26, 2019, 4 pages.
(Continued)

*Primary Examiner* — Rachel T Sippel
*Assistant Examiner* — Gwynneth L Howell
(74) *Attorney, Agent, or Firm* — BAYES PLLC

(57) ABSTRACT

The disclosure provides an airway anomaly detection method and a ventilation device thereof. The method may include acquiring a ventilation parameter, where the ventilation parameter includes at least one of an airway pressure and airway flow; detecting, according to a change of the ventilation parameter, whether an airway anomaly event
(Continued)

```
┌─────────────────────────────────────────────────────────────┐
│  Acquire a ventilation parameter, wherein the ventilation    │  S101
│  parameter comprises at least one of an airway pressure and  │
│  an airway flow                                              │
└─────────────────────────────────────────────────────────────┘
                              │
                              ▼
┌─────────────────────────────────────────────────────────────┐
│  Determine, according to a change of the ventilation         │  S102
│  parameter, whether an airway anomaly event occurs           │
└─────────────────────────────────────────────────────────────┘
                              │
                              ▼
┌─────────────────────────────────────────────────────────────┐
│  When it is determined that the airway anomaly event occurs, │  S103
│  output an airway anomaly event prompt                       │
└─────────────────────────────────────────────────────────────┘
``` occurs; and when it is determined that the airway anomaly event occurs, outputting an airway anomaly event prompt.

18 Claims, 4 Drawing Sheets

(52) U.S. Cl.
CPC ... *A61M 2016/003* (2013.01); *A61M 2205/18* (2013.01); *A61M 2205/581* (2013.01); *A61M 2205/587* (2013.01)

(58) Field of Classification Search
CPC ............ A61M 2205/18; A61M 16/026; A61M 16/1065; A61M 16/107; A61M 2016/0039; A61M 2016/0042; A61M 2016/0036; A61M 2205/502; A61M 2230/46; A61M 16/16; A61M 16/0808; A61B 5/085; A61B 5/746
See application file for complete search history.

(56) References Cited

U.S. PATENT DOCUMENTS

| | | | | |
|---|---|---|---|---|
| 6,668,824 B1* | 12/2003 | Isaza | ................. | A61M 16/0051 128/204.23 |
| 7,882,834 B2* | 2/2011 | Gradon | ............. | A61M 16/0069 128/204.23 |
| 2003/0010339 A1* | 1/2003 | Banner | ............... | A61M 16/026 128/204.18 |
| 2004/0097821 A1* | 5/2004 | Blomberg | ............. | A61M 16/00 128/204.23 |
| 2008/0121232 A1* | 5/2008 | Cewers | ............... | A61M 16/024 128/204.22 |
| 2008/0234595 A1* | 9/2008 | Ranieri | .................. | A61B 5/085 600/538 |
| 2008/0257350 A1* | 10/2008 | Huang | ................ | A61M 16/205 128/205.13 |
| 2009/0241951 A1* | 10/2009 | Jafari | .................. | A61M 16/026 128/204.21 |
| 2011/0196251 A1* | 8/2011 | Jourdain | ............... | A61M 16/04 128/204.21 |
| 2014/0276173 A1* | 9/2014 | Banner | ............. | A61M 16/0434 600/533 |
| 2015/0120067 A1 | 4/2015 | Wing et al. | | |
| 2018/0001042 A1* | 1/2018 | Albanese | ............ | A61M 16/026 |
| 2018/0036460 A1 | 2/2018 | Bullock et al. | | |
| 2019/0015614 A1* | 1/2019 | Alahmadi | .............. | A61B 5/082 |
| 2020/0046924 A1* | 2/2020 | Truschel | ............ | A61M 16/024 |

FOREIGN PATENT DOCUMENTS

| | | |
|---|---|---|
| CN | 103169476 A | 6/2013 |
| CN | 101337101 A | 1/2019 |

OTHER PUBLICATIONS

Extended European Search Report issued in related European Application No. 18931256.4, mailed Feb. 7, 2022, 10 pages.

* cited by examiner

AIRWAY ANOMALY RECOGNITION METHOD, VENTILATION DEVICE, AND STORAGE MEDIUM

CROSS-REFERENCE TO RELATED APPLICATIONS

This application is a bypass continuation of Patent Cooperation Treaty Application No. PCT/CN2018/101595, filed Aug. 21, 2018, the content of which is incorporated herein by reference in its entirety.

TECHNICAL FIELD

Embodiments of the disclosure relate to a technical field of medical devices, and in particular, to an airway anomaly recognition method, a ventilation device, and a storage medium.

BACKGROUND

Ventilation devices such as ventilators are devices that may effectively replace, control or change people's normal physiological breathing, increase pulmonary ventilation, improve respiratory function, reduce respiratory consumption and save cardiac reserve.

During the process of mechanical ventilation by means of the ventilator, some airway anomaly events are prone to occur, including: due to the use of a humidifier in a respiration circuit, it easily causes the condensation of water vapor and accumulation in the pipeline and hinders the ventilation; the accumulation of a patient's airway secretions in the airway causes the airway resistance to increase and the airway to be blocked, which hinders the ventilation; and bacterial filters are installed at a gas supply end and an expiration end of the ventilator to prevent infection. After long-term use, the filters will be wet by the water vapor in the patient's breathing gas, which will lead to an increase in the filter resistance and hinder the ventilation.

The airway anomaly events mentioned above will cause the ventilator to fail to perform ventilation normally, thus affecting the therapeutic effect.

SUMMARY

To solve the above technical problems, embodiments of the disclosure provide an airway anomaly recognition method, a ventilation device, and a storage medium, such that according to a change of a ventilation parameter, a specific airway anomaly event may be recognized and a prompt is made, which facilitates the handling of the airway anomaly event by an operator and ensures the normal ventilation of the ventilation device, thereby improving the treatment effect.

The technical solutions of the embodiments of the disclosure may be implemented as follows:

An embodiment of the disclosure provides an airway anomaly recognition method, where the method includes:
  acquiring a ventilation parameter, the ventilation parameter includes at least one of an airway pressure and an airway flow;
  recognizing, according to a change of the ventilation parameter, whether an airway anomaly event occurs; and
  outputting an airway anomaly event prompt when it is recognized that the airway anomaly event occurs.

In one embodiment, the airway anomaly event includes one or more of a water accumulation in circuit, a sputum accumulation and a circuit resistance increase.

In one embodiment, recognizing, according to a change of the ventilation parameter, whether an airway anomaly event occurs includes:
  determining, when the ventilation parameter continuously jitters, that a water accumulation in circuit occurs.

In one embodiment, recognizing, according to a change of the ventilation parameter, whether an airway anomaly event occurs includes:
  performing a spectral analysis on the ventilation parameter; and determining, if a high-frequency component of the ventilation parameter is greater than a preset first threshold, that a water accumulation in circuit occurs.

In one embodiment, recognizing, according to a change of the ventilation parameter, whether an airway anomaly event occurs includes:
  performing curve fitting on the ventilation parameter;
  calculating an error between the fitted curve and the ventilation parameter; and
  determining, if the error is greater than a preset second threshold, that a water accumulation in circuit occurs.

In one embodiment, recognizing, according to a change of the ventilation parameter, whether an airway anomaly event occurs includes:
  calculating an airway resistance through the airway pressure and the airway flow; and
  if the airway resistance increases, determining that a sputum accumulation occurs.

In one embodiment, the airway pressure includes an inspiratory pressure and an expiratory pressure, and recognizing, according to a change of the ventilation parameter, whether an airway anomaly event occurs includes:
  determining, through the inspiratory pressure and the expiratory pressure, whether a circuit resistance increase occurs.

In one embodiment, determining, through the inspiratory pressure and the expiratory pressure, whether a circuit resistance increase occurs includes:
  calculating a current pipeline pressure drop through the inspiratory pressure and the expiratory pressure; and
  determining, if a difference between the current pipeline pressure drop and an initial pipeline pressure drop is greater than a preset third threshold, that a circuit resistance increase occurs.

In one embodiment, determining, through the inspiratory pressure and the expiratory pressure, whether a circuit resistance increase occurs includes:
  calculating a change in pressure drop of the pipeline through the inspiratory pressure and the expiratory pressure; and
  determining, if an increase value in pressure drop of the pipeline is greater than a preset fourth threshold, that a circuit resistance increase occurs.

In the above solution, the airway flow includes an inspiratory flow and an expiratory flow, the inspiratory pressure is calculated through the inspiratory flow, and the expiratory pressure is calculated through the expiratory flow.

An embodiment of the disclosure provides an airway anomaly recognition apparatus, where the apparatus includes:
  an acquisition module for acquiring a ventilation parameter, the ventilation parameter includes at least one of an airway pressure and an airway flow;

a recognition module for recognizing, according to a change of the ventilation parameter, whether an airway anomaly event occurs; and an output module for outputting an airway anomaly event prompt when it is recognized that the airway anomaly event occurs.

In one embodiment, the airway anomaly event includes one or more of a water accumulation in circuit, a sputum accumulation and a circuit resistance increase.

In one embodiment, recognizing, by the recognition module according to a change of the ventilation parameter, whether an airway anomaly event occurs includes:

determining, when the ventilation parameter continuously jitters, that a water accumulation in circuit occurs.

In one embodiment, recognizing, by the recognition module according to a change of the ventilation parameter, whether an airway anomaly event occurs includes:

performing a spectral analysis on the ventilation parameter; and determining, if a high-frequency component of the ventilation parameter is greater than a preset first threshold, that a water accumulation in circuit occurs.

In one embodiment, recognizing, by the recognition module according to a change of the ventilation parameter, whether an airway anomaly event occurs includes:

performing curve fitting on the ventilation parameter;

calculating an error between the fitted curve and the ventilation parameter; and determining, if the error is greater than a preset second threshold, that a water accumulation in circuit occurs.

In one embodiment, recognizing, by the recognition module according to a change of the ventilation parameter, whether an airway anomaly event occurs includes:

calculating an airway resistance through the airway pressure and the airway flow; and if the airway resistance increases, determining that a sputum accumulation occurs.

In one embodiment, the airway pressure includes an inspiratory pressure and an expiratory pressure, and recognizing, by the recognition module according to a change of the ventilation parameter, whether an airway anomaly event occurs includes:

determining, through the inspiratory pressure and the expiratory pressure, whether a circuit resistance increase occurs.

In one embodiment, determining, by the recognition module through the inspiratory pressure and the expiratory pressure, whether a circuit resistance increase occurs includes:

calculating a current pipeline pressure drop through the inspiratory pressure and the expiratory pressure; and determining, if a difference between the current pipeline pressure drop and an initial pipeline pressure drop is greater than a preset third threshold, that a circuit resistance increase occurs.

In one embodiment, determining, by the recognition module through the inspiratory pressure and the expiratory pressure, whether a circuit resistance increase occurs includes:

calculating a change in pressure drop of the pipeline through the inspiratory pressure and the expiratory pressure; and determining, if an increase value in pressure drop of the pipeline is greater than a preset fourth threshold, that a circuit resistance increase occurs.

In one embodiment, the airway flow includes an inspiratory flow and an expiratory flow, the inspiratory pressure is calculated through the inspiratory flow, and the expiratory pressure is calculated through the expiratory flow.

One embodiment of the disclosure provides a ventilation device including the above airway anomaly recognition apparatus, the ventilation device including a gas source, an inspiratory limb, an expiratory limb, a display, and a controller;

the gas source provides a gas during mechanical ventilation;

the inspiratory limb is connected to the gas source and provides an inspiratory path during the mechanical ventilation;

the expiratory limb provides an expiratory path during the mechanical ventilation;

the airway anomaly recognition apparatus is connected to the inspiratory limb, the expiratory limb and the controller;

the airway anomaly recognition apparatus recognizes an airway anomaly event during the mechanical ventilation;

the controller is further connected to the gas source and controls the process of the mechanical ventilation; and the display is connected to the controller and displays a respiratory waveform during the mechanical ventilation.

An embodiment of the disclosure provides a computer-readable storage medium, the computer-readable storage medium stores an airway anomaly recognition program, and the airway anomaly recognition program is executable by a processor to implement the above airway anomaly recognition method.

It may be seen that in the technical solution of the embodiments of the disclosure, the airway anomaly recognition apparatus acquires a ventilation parameter, the ventilation parameter includes at least one of an airway pressure and an airway flow; recognizes, according to a change of the ventilation parameter, whether an airway anomaly event occurs; and outputs an airway anomaly event prompt when it is recognized that the airway anomaly event occurs. That is to say, in the technical solution provided according to the embodiments of the disclosure, according to a change of the ventilation parameter, a specific airway anomaly event may be recognized and a prompt is made, which facilitates the handling of the airway anomaly event by an operator and ensures the normal ventilation of the ventilation device, thereby improving the treatment effect.

DETAILED DESCRIPTION

In order to understand the features and technical contents of embodiments of the disclosure in more detail, the implementation of the embodiments of the disclosure will be described below in detail with reference to the accompanying drawings, which are for reference and illustration only, and are not intended to limit the embodiments of the disclosure.

Embodiment I

Figure 1:
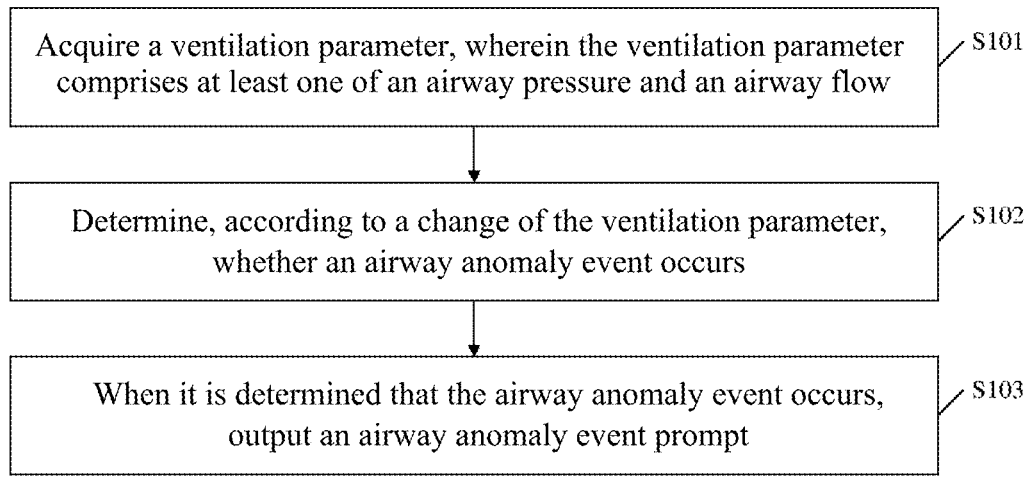
FIG. 1 is a schematic flow chart of an airway anomaly recognition method provided according to an embodiment of the disclosure.

An embodiment of the disclosure provides an airway anomaly recognition method. FIG. 1 is a schematic flow chart of the airway anomaly recognition method provided according to an embodiment of the disclosure. As shown in FIG. 1, the method mainly includes the following steps:

S101: acquiring a ventilation parameter, the ventilation parameter includes at least one of an airway pressure and an airway flow.

In one embodiment of the disclosure, the airway anomaly recognition apparatus may acquire the ventilation parameter in real time during the process of performing mechanical ventilation by a ventilation device.

It should be noted that, in one embodiment of the disclosure, the ventilation parameter includes at least one of the airway pressure and the airway flow.

It should be noted that, in one embodiment of the disclosure, the airway anomaly recognition apparatus is a part of the ventilation device, and the ventilation device is a medical device, such as a ventilator and an anesthesia machine, with a ventilation function. The specific ventilation device is not limited in the embodiments of the disclosure.

It should be noted that, in one embodiment of the disclosure, the airway anomaly recognition apparatus continuously acquires the ventilation parameter.

S102: recognizing, according to a change of the ventilation parameter, whether an airway anomaly event occurs.

In one embodiment of the disclosure, after acquiring the ventilation parameter, the airway anomaly recognition apparatus recognizes, according to a change of the ventilation parameter, whether the airway anomaly event occurs.

It should be noted that, in one embodiment of the disclosure, the airway anomaly event includes one or more of a water accumulation in circuit, a sputum accumulation and a circuit resistance increase.

It may be understood that in one embodiment of the disclosure, the ventilation device recognizes, according to a change of the ventilation parameter, whether a water accumulation in circuit occurs as the ventilation device is generally used with a humidifier, water vapor easily condenses in the pipeline and the accumulation of a large amount of water in the pipeline will hinder the ventilation. The ventilation device recognizes, according to a change of the ventilation parameter, whether a sputum accumulation occurs, as a sputum accumulation in a patient's respiratory tract will lead to an increase in the airway resistance, which will hinder the ventilation. The ventilation device recognizes, according to a change of the ventilation parameter, whether a circuit resistance increase occurs, as bacterial filters are installed at an inspiration end and an expiration end of the ventilation device, and gases exhaled by the patient are wet gases, which will wet the filters after condensation and result in an excessive pipeline resistance, thus hindering the ventilation.

In one embodiment of the disclosure, the step of recognizing, by the airway anomaly recognition apparatus according to a change of the ventilation parameter, whether an airway anomaly event occurs includes: determining, when the ventilation parameter continuously jitters, that a water accumulation in circuit occurs.

It should be noted that, in one embodiment of the disclosure, when a water accumulation in circuit occurs in the ventilation device, the accumulated water in the pipeline will flow along with the flow of gas in the pipeline. At this point, both the airway pressure and airway flow acquired by the airway anomaly recognition apparatus always jitter up and down, but under normal conditions, neither of the airway pressure and airway flow acquired by the airway anomaly recognition apparatus jitters up and down. Therefore, as long as the ventilation device detects that one of the airway pressure or the airway flow always jitters up and down, it may be determined that a water accumulation in circuit occurs.

As an example, in one embodiment of the disclosure, when the value of the airway pressure or the airway flow always increases or decreases at a fast frequency, i.e., when jitter occurs, the airway anomaly recognition apparatus may determine that water accumulates in the pipeline.

Figure 2A:
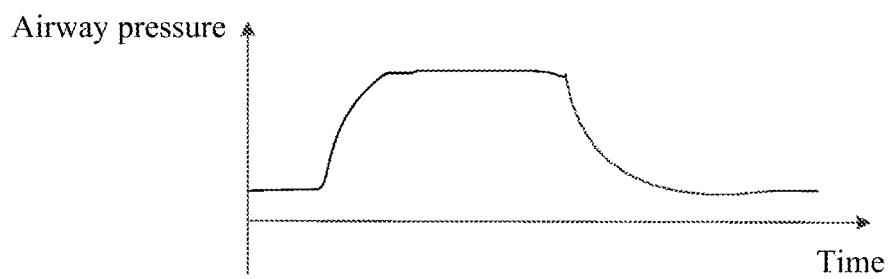
FIG. 2(a) is an exemplary schematic waveform diagram of airway pressure-time under normal conditions provided according to an embodiment of the disclosure.
Figure 2B:
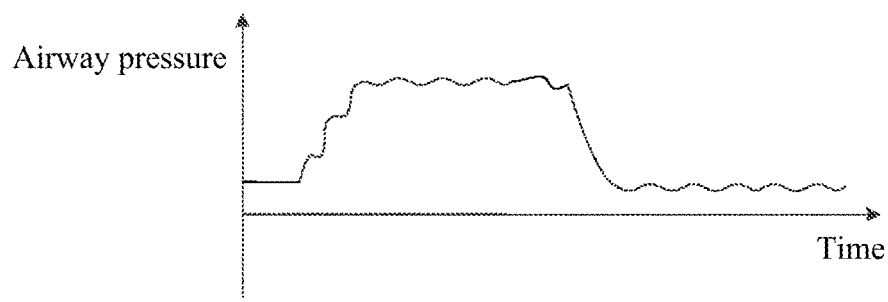
FIG. 2(b) is an exemplary schematic waveform diagram of airway pressure-time during a water accumulation in circuit provided according to an embodiment of the disclosure.

FIG. 2(*a*) is an exemplary schematic waveform diagram of airway pressure-time under normal conditions provided according to an embodiment of the disclosure. As shown in FIG. 2(*a*), under normal conditions, when the airway pressure does not jitter, the waveform of airway pressure-time is relatively smooth.

FIG. 2(*b*) is an exemplary schematic waveform diagram of airway pressure-time during a water accumulation in circuit provided according to an embodiment of the disclosure. As shown in FIG. 2(*b*), when water accumulates in the pipeline in the ventilation device, the airway pressure always jitters up and down, and the waveform of airway pressure-time is unsmooth.

Figure 3A:
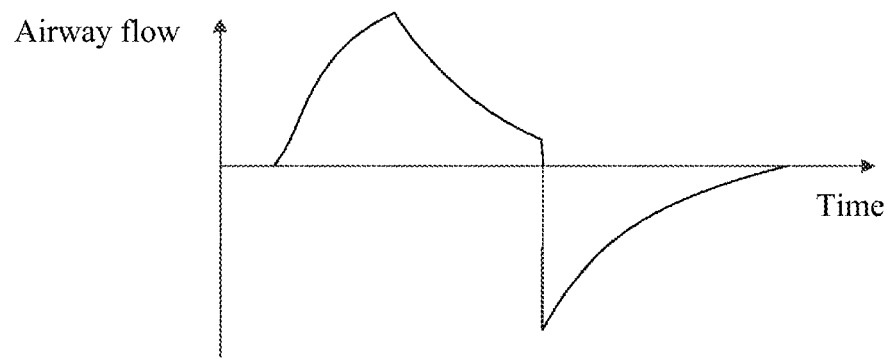
FIG. 3(a) is an exemplary schematic waveform diagram of airway flow-time under normal conditions provided according to an embodiment of the disclosure.
Figure 3B:
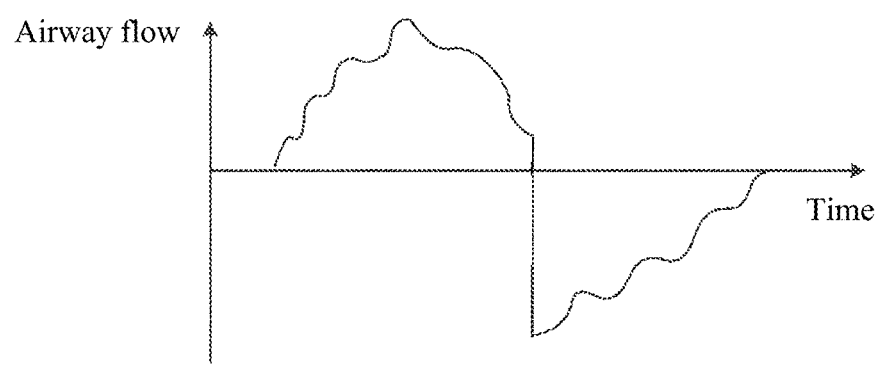
FIG. 3(b) is an exemplary schematic waveform diagram of the airway flow-time during a water accumulation in circuit provided according to an embodiment of the disclosure.

FIG. 3(*a*) is an exemplary schematic waveform diagram of airway flow-time under normal conditions provided according to an embodiment of the disclosure. As shown in FIG. 3(*a*), under normal conditions, when the airway flow does not jitter, the waveform of airway flow-time is relatively smooth.

FIG. 3(*b*) is an exemplary schematic waveform diagram of gas flow speed-time during a water accumulation in circuit provided according to an embodiment of the disclosure. As shown in FIG. 3(*b*), when water accumulates in the pipeline in the ventilation device, the airway flow always jitters up and down, and the waveform of airway flow-time is unsmooth.

It should be noted that, in one embodiment of the disclosure, when the ventilation device is in any ventilation mode, both the airway pressure and the airway flow will continuously jitter as long as a water accumulation in circuit occurs, and the ventilation device only needs to detect a change of one of the airway pressure and the airway flow.

In one embodiment of the disclosure, the step of recognizing, by the airway anomaly recognition apparatus according to a change of the ventilation parameter, whether an airway anomaly event occurs includes: performing spectral analysis on the ventilation parameter; and if a high-frequency component of the ventilation parameter is greater than a preset first threshold, determining that a water accumulation in circuit occurs.

It should be noted that, in one embodiment of the disclosure, the airway anomaly recognition apparatus performs the spectral analysis on the ventilation parameter, that is, transforming the ventilation parameter from time domain to frequency domain for analysis. For example, Fourier transform is performed on the acquired airway pressure or airway flow, i.e., the data in the time domain, to obtain corresponding frequency domain data, specifically the high-frequency component of the airway pressure or the airway flow. The specific spectral analysis method is not limited in the embodiments of the disclosure.

It should be noted that, in one embodiment of the disclosure, components greater than a certain value of the ventilation parameter may be determined as high-frequency components, for example, components greater than 20 HZ of the ventilation parameter may be determined as high-frequency components. The specific limit value of the high-frequency component is not limited in the embodiments of the disclosure.

It should be noted that, in one embodiment of the disclosure, during the whole mechanical ventilation, when a water accumulation in circuit does not occur to the ventilation device, the ventilation parameter changes steadily because the flow of the gas is not continuously hindered and oscillated, which is reflected in that fewer high-frequency components are present in the results of the spectral analysis of the ventilation parameter. However, when a water accumulation in circuit occurs to the ventilation device, the ventilation parameter changes drastically because the flow of the gas is continuously hindered and oscillated, which is reflected in that more high-frequency components are present in the results of the spectral analysis of the ventilation parameter. Therefore, if the high-frequency components of the ventilation parameter exceed the preset first threshold, it is determined that a water accumulation in circuit occurs.

It should be noted that, in one embodiment of the disclosure, the first threshold may be a value preset autonomously by a user, or may be a value stored by the ventilation device by default, and the specific first threshold is not limited in the embodiments of the disclosure.

As an example, in one embodiment of the disclosure, the airway anomaly recognition apparatus performs spectral analysis on the airway pressure to obtain a high-frequency component of the airway pressure, and if the high-frequency component of the airway pressure is greater than a first threshold A, it is determined that a water accumulation in circuit occurs.

As an example, in one embodiment of the disclosure, the airway anomaly recognition apparatus performs the spectral analysis on the airway flow to obtain a high-frequency component of the airway flow, and if the high-frequency component of the airway flow is greater than a first threshold B, it is determined that a water accumulation in circuit occurs.

In one embodiment of the disclosure, the step of recognizing, by the airway anomaly recognition apparatus according to a change of the ventilation parameter, whether an airway anomaly event occurs includes: performing curve fitting on the ventilation parameter; calculating an error between the fitted curve and the ventilation parameter; and determining, if the error is greater than a preset second threshold, that a water accumulation in circuit occurs.

It should be noted that in one embodiment of the disclosure, after acquiring the ventilation parameter, the airway anomaly recognition apparatus may also perform the curve fitting on the ventilation parameter to obtain the fitted curve, but there is a certain error between the fitted curve and the actual ventilation parameter. If the calculated error between the fitted curve and the ventilation parameter is great, namely greater than the preset second threshold, it indicates that the ventilation parameter actually deviates from the fitted curve to a large extent, that is, the ventilation parameter continuously jitters up and down to a large extent, and thus it is determined that a water accumulation in circuit occurs.

It should be noted that, in one embodiment of the disclosure, the second threshold may be a value preset autonomously by the user, or may be a value stored by the ventilation device by default, and the specific second threshold is not limited in the embodiments of the disclosure.

Figure 4:
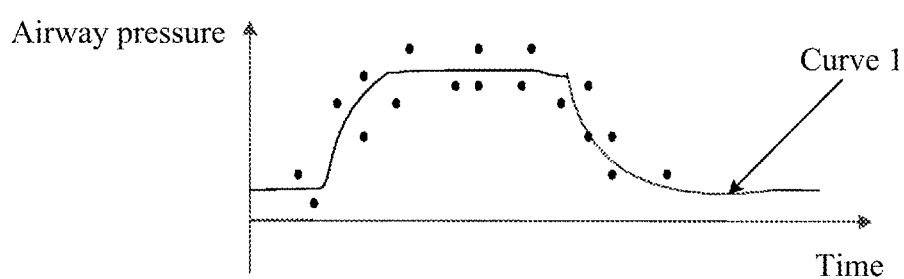
FIG. 4 is an exemplary fitted curve of the airway pressure provided according to an embodiment of the disclosure.

FIG. 4 is an exemplary fitted curve of the airway pressure provided according to an embodiment of the disclosure. As shown in FIG. 4, the airway anomaly recognition apparatus performs the curve fitting on the airway pressure, specifically fits numerical points corresponding to the acquired airway pressure shown in the figure to obtain a curve 1, then an error between the curve 1 and the numerical points may be calculated, and if the error is greater than the preset second threshold, it is determined that a water accumulation in circuit occurs.

In one embodiment of the disclosure, the step of recognizing, by the airway anomaly recognition apparatus according to a change of the ventilation parameter, whether an airway anomaly event occurs includes: calculating the airway resistance according to the airway pressure and the airway flow; and if the airway resistance increases, determining that a sputum accumulation occurs.

It should be noted that, in one embodiment of the disclosure, after sputum in a patient's respiratory tract gradually accumulates, the ventilation will be hindered, and at this point, the airway resistance will gradually increase, but under normal conditions, the sputum in the patient's respiratory tract does not accumulate, and the airway resistance remains stable and constant.

It should be noted that, in one embodiment of the disclosure, the airway resistance refers to a pressure difference generated per unit flow in the airway, so the airway anomaly recognition apparatus may calculate the airway resistance through the acquired airway pressure and airway flow.

It should be noted that, in one embodiment of the disclosure, the airway pressure includes an inspiratory pressure and an expiratory pressure, the gas flow speed includes an inspiratory flow and an expiratory flow, the inspiratory pressure may be calculated through the inspiratory flow, the expiratory pressure may be calculated through the expiratory flow, and the inspiratory pressure and the expiratory pressure may also be directly obtained by relevant sensors on the ventilation device.

In one embodiment of the disclosure, the step of recognizing, by the airway anomaly recognition apparatus according to a change of the ventilation parameter, whether a circuit resistance increase occurs includes: determining, through the inspiratory pressure and the expiratory pressure, whether a circuit resistance increase occurs.

In one embodiment of the disclosure, the airway anomaly recognition apparatus calculates a current pipeline pressure drop through the inspiratory pressure and the expiratory pressure; and determines, if a difference between the current pipeline pressure drop and an initial pipeline pressure drop is greater than a preset third threshold, that a circuit resistance increase occurs.

It should be noted that, in one embodiment of the disclosure, the third threshold may be a value preset autonomously by a user, or may be a value stored by the ventilation device by default, and the specific third threshold is not limited in the embodiments of the disclosure.

It should be noted that, in one embodiment of the disclosure, a pressure drop calculation model may be preset to calculate the initial pipeline pressure drop. However, because different pipelines have different properties, a resistance coefficient included in the preset pressure drop calculation model also needs to be determined according to an actual situation. Specifically, a resistance coefficient model may be preset, and a resistance coefficient in the preset resistance coefficient model is determined by using a relevant test method, and then the resistance coefficient in the preset pressure drop calculation model is further calculated according to the resistance coefficient in the preset resistance coefficient model.

In one embodiment of the disclosure, a patient port of a patient pipeline in the ventilation device may be closed, a gas is supplied to an inspiratory limb at a preset test flow speed, then an inspiratory test pressure and an expiratory test pressure are acquired, and the resistance coefficient in the preset resistance coefficient model is calculated according to the test flow speed, the inspiratory test pressure, the expiratory test pressure and the preset resistance coefficient model. The resistance coefficient in the preset pressure drop calculation model is determined according to the resistance coefficient in the preset resistance coefficient model.

Figure 5:
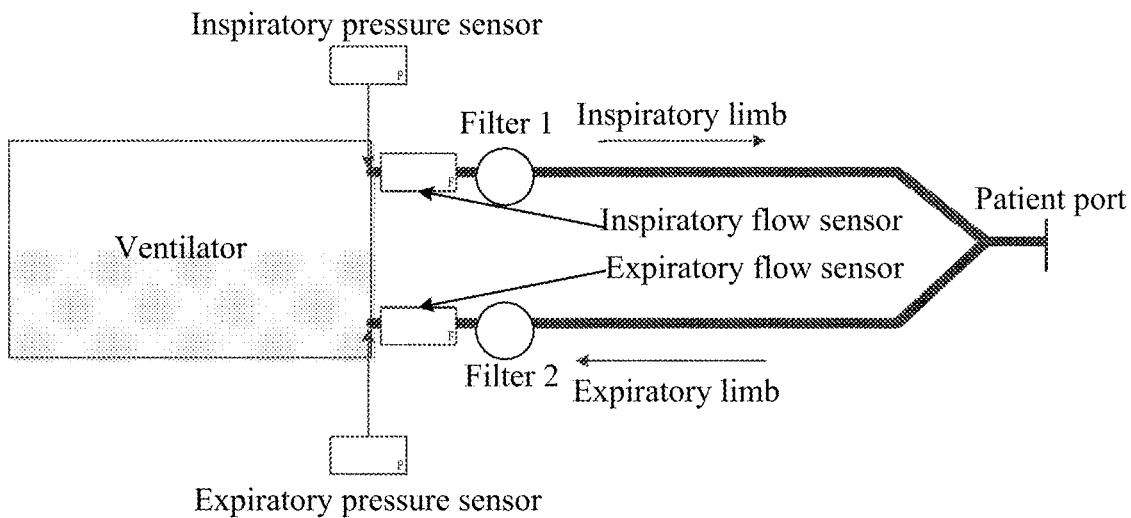
FIG. 5 is an exemplary schematic diagram of connections of a ventilation device during a test provided according to an embodiment of the disclosure.

FIG. 5 is an exemplary schematic diagram of connections of the ventilation device in a test process provided according to an embodiment of the disclosure. As shown in FIG. 5, during the test, the patient port used by the patient is closed and blocked, which may ensure that the ventilation device supplies the gas through the inspiratory limb, and the gas flows directly from the inspiratory limb to the expiratory limb and then flows out. The inspiratory limb is equipped with a filter 1, an inspiratory flow sensor and an inspiratory pressure sensor, and the expiratory limb is equipped with a filter 2, an expiratory flow sensor and an expiratory pressure sensor. The inspiratory flow sensor is configured to obtain an inspiratory flow, the expiratory flow sensor is configured to obtain an expiratory flow, the inspiratory pressure sensor is configured to obtain an inspiratory pressure, and the expiratory pressure sensor is configured to obtain an expiratory pressure. During the test, the ventilation device uses three test flow speeds F1, F2 and F3, to supply the gas to the inspiratory limb. The inspiratory flow of the inspiratory limb and the expiratory flow of the expiratory limb each are test flow speeds. Inspiratory test pressures Pi1, Pi2 and Pi3 and expiratory test pressures Pe1, Pe2 and Pe3 may be acquired respectively. The data is substituted into the preset resistance coefficient model for calculation, and the resistance coefficient in the preset resistance coefficient model may be obtained. The preset resistance coefficient model is shown in equation (1):

$$\Delta Pressure = a \times Flow^2 + b \times Flow + c \quad (1)$$

$\Delta$Pressure is a difference between the inspiratory test pressure and the expiratory test pressure, Flow is the test flow speed, and a, b and c are resistance coefficients in the preset resistance coefficient model. Therefore, the above F1, Pi1 and Pe1, F2, Pi2 and Pe2, and F3, Pi3 and Pe3 are respectively substituted into equation (1) as follows:

$$Pi1 - Pe1 = a \times F1^2 + b \times F1 + c \quad (2)$$

$$Pi2 - Pe2 = a \times F2^2 + b \times F2 + c \quad (3)$$

$$Pi3 - Pe3 = a \times F3^2 + b \times F3 + c \quad (4)$$

Specific values of a, b and c may be calculated according to the combination of equations (2), (3) and (4).

It should be noted that, in one embodiment of the disclosure, more than three test flow speeds may further be included, and the ventilation device may more accurately obtain the resistance coefficients in the resistance coefficient model by a fitting method through more tests of the test flow speed. In addition, it is also possible to reserve only a by adaptively removing b and c by simplification, such that a is calculated through one test flow speed. It may be understood that removing b and c by simplification has a certain impact on the accuracy of the preset pressure drop calculation model finally determined by the resistance coefficient of the resistance coefficient model, but the ventilation device may still recognize an event of an excessive filter resistance.

It should be noted that, in one embodiment of the disclosure, because the expiratory limb and the inspiratory limb are substantially symmetrical, the resistance coefficient in the preset pressure drop calculation model may be determined as ½ of the resistance coefficient in the preset resistance coefficient model, and the preset pressure drop calculation model is shown in equation (5):

$$\Delta Ptube = \frac{a}{2} \times Fi^2 + \frac{b}{2} \times Fi + \frac{a}{2} \times Fe^2 + \frac{b}{2} \times Fe + c \quad (5)$$

$\Delta$Ptube is a target pipeline pressure drop, Fi is an inspiratory flow, and Fe is an expiratory flow. After the resistance coefficients a, b and c in the preset resistance coefficient model are calculated by using the above method, the specific data of a, b and c may be substituted into equation (5) to determine the resistance coefficient in the preset pressure drop calculation model.

Figure 6:
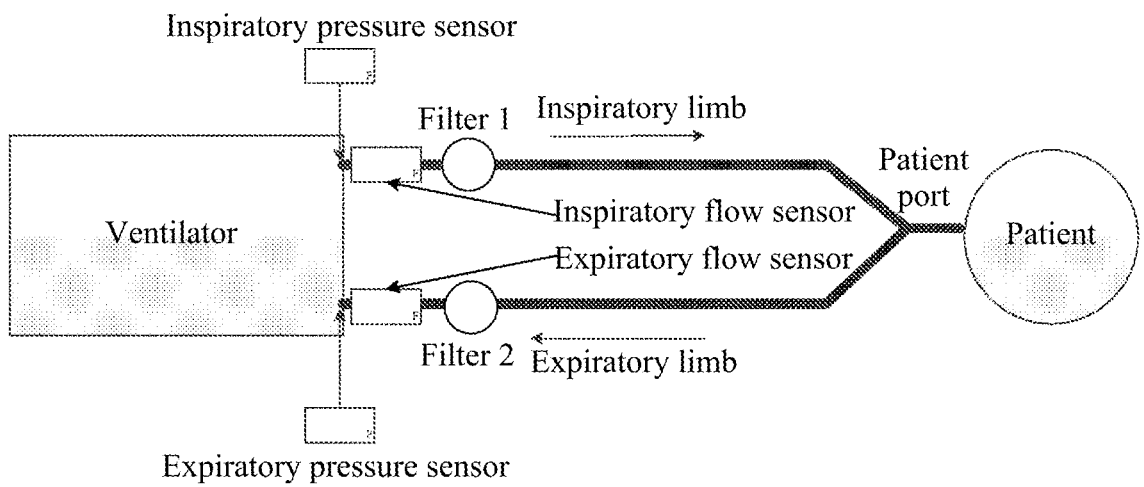
FIG. 6 is an exemplary schematic diagram of the connections of the ventilation device during ventilation provided according to an embodiment of the disclosure.

FIG. 6 is an exemplary schematic diagram of the connections of the ventilation device during ventilation provided according to an embodiment of the disclosure. As shown in FIG. 6, during ventilation, the ventilation device is connected to the patient via a patient port. If the flow speed at which the inhaled gas flows through the inspiratory limb is Fa and the flow speed at which the exhaled gas flows through the expiratory limb is Fb, the initial pipeline pressure drop may be calculated by substituting Fa and Fb into equation (5). At the same time, the ventilation device acquires an inspiratory pressure Pia and an expiratory pressure Pib by means of the inspiratory pressure sensor and the expiratory pressure sensor, determines a difference between the inspiratory pressure Pia and the expiratory pressure Pib as the current pipeline pressure drop, compares the current pipeline pressure drop with the initial pipeline pressure drop, and determines, if a difference between the current pipeline pressure drop and the initial pipeline pressure drop is greater than a preset third threshold, that a circuit resistance increase occurs.

It may be understood that, in one embodiment of the disclosure, the difference between the current pipeline pressure drop and the initial pipeline pressure drop is actually the pressure drop across the filter on the ventilation device. Therefore, if the difference between the current pipeline pressure drop and the initial pipeline pressure drop is greater than the preset third threshold, that is, the pressure drop across the filter is too great, it indicates that the filter resistance is relatively great.

In one embodiment of the disclosure, the step of determining, by the airway anomaly recognition apparatus through the inspiratory pressure and the expiratory pressure, whether a circuit resistance increase occurs further includes: calculating a change in pressure drop of the pipeline through the inspiratory pressure and the expiratory pressure; and determining, if an increase value in pressure drop of the pipeline is greater than a preset fourth threshold, that a circuit resistance increase occurs.

It should be noted that, in one embodiment of the disclosure, the fourth threshold may be a value preset autonomously by the user, or may be a value stored by the ventilation device by default, and the specific fourth threshold is not limited in the embodiments of the disclosure.

It should be noted that, in one embodiment of the disclosure, since the airway anomaly recognition apparatus acquires the inspiratory pressure and the expiratory pressure in real time, the difference between the inspiratory pressure and the expiratory pressure may be calculated in real time, and the pressure drop across the pipeline at each moment is obtained, so as to calculate the change in pressure drop of the pipeline.

As an example, in one embodiment of the disclosure, the airway anomaly recognition apparatus calculates the difference between the inspiratory pressure and the expiratory pressure as a1 at a first moment, and calculates the difference between the inspiratory pressure and the expiratory pressure as a2 at a second moment, and then may calculate the change in pressure drop of the pipeline as a2-a1.

It may be understood that, under normal conditions, when the filter is not wet or slightly wet, the pressure drop across the pipeline is generally unchanged, and even if it increases, the increase value in pressure drop of the pipeline is relatively small, while when the filter is wet seriously, the change in pressure drop of the pipeline is great, and the increase value in pressure drop of the pipeline is also great. Therefore, when the increase value in pressure drop of the pipeline is greater than the preset fourth threshold, it is determined that a circuit resistance increase occurs.

As an example, in one embodiment of the disclosure, the airway anomaly recognition apparatus calculates the change in pressure drop of the pipeline through the inspiratory pressure and the expiratory pressure, and when the obtained pressure drop increase value of the pipeline is M, and M is greater than a preset fourth threshold N, it is determined that a circuit resistance increase occurs.

S103: outputting an airway anomaly event prompt when an airway anomaly event is recognized.

In one embodiment of the disclosure, after recognizing, according to a change of the ventilation parameter, whether the airway anomaly event occurs, the airway anomaly recognition apparatus outputs the airway anomaly event prompt when recognizing the airway anomaly event.

It may be understood that, in one embodiment of the disclosure, after recognizing whether an airway anomaly event occurs, the airway anomaly recognition apparatus may recognize no airway anomaly event, that is, recognizing no event of a water accumulation in circuit, a sputum accumulation and a circuit resistance increase, at this point, the airway anomaly recognition apparatus does not need to output the airway anomaly event prompt.

In one embodiment of the disclosure, outputting the airway anomaly event prompt when the airway anomaly recognition apparatus recognizes that an airway anomaly event occurs includes: controlling an indicator light corresponding to the airway anomaly event to blink; or giving an alarm prompt tone corresponding to the airway anomaly event.

As an example, in one embodiment of the disclosure, a first indicator light corresponding to a water accumulation in circuit, a second indicator light corresponding to a sputum accumulation, and a third indicator light corresponding to a circuit resistance increase are provided. When the airway anomaly recognition apparatus recognizes that a water accumulation in circuit occurs, the first indicator light is controlled to blink, and medical care personnel may timely drain the water from the pipeline after seeing the blinking of the first indicator light. When the airway anomaly recognition apparatus recognizes that a sputum accumulation occurs, the second indicator light is controlled to blink, and the medical care personnel may timely help the patient to eliminate sputum after seeing the blinking of the second indicator light blink. When the airway anomaly recognition apparatus recognizes that a circuit resistance increase occurs, the third indicator light is controlled to blink, and the medical care personnel may timely replace the filter after seeing the blinking of the third indicator light blink.

As an example, in one embodiment of the disclosure, the alarm prompt tone corresponding to a water accumulation in circuit is buzz. When the airway anomaly recognition apparatus recognizes that a water accumulation in circuit occurs, the buzz is emitted, and the medical care personnel may timely drain the water from the pipeline after hearing the emitted buzz.

It should be noted that, in one embodiment of the disclosure, the airway anomaly event prompt output by the airway anomaly recognition apparatus may also include other types of prompts. For example, a text prompt of a related airway anomaly event is output and displayed on a display of the ventilation device. The specific airway anomaly event prompt is not limited in the embodiments of the disclosure.

An embodiment of the disclosure provides an airway anomaly recognition method. The airway anomaly recognition apparatus acquires a ventilation parameter, the ventilation parameter includes at least one of an airway pressure and an airway flow; recognizes, according to a change of the ventilation parameter, whether an airway anomaly event occurs; and outputs an airway anomaly event prompt when it is recognized that the airway anomaly event occurs. That is to say, in the technical solution provided according to one embodiment of the disclosure, according to a change of the ventilation parameter, a specific airway anomaly event may be recognized and a prompt is made, which facilitates the handling of the airway anomaly event by an operator and ensures the normal ventilation of the ventilation device, thereby improving the treatment effect.

Embodiment II

Figure 7:
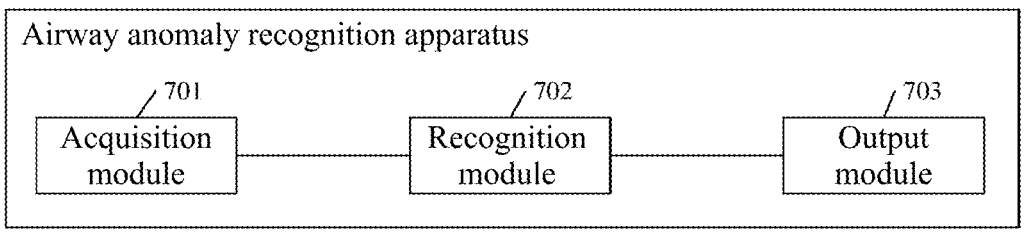
FIG. 7 is a schematic structural diagram of an airway anomaly recognition apparatus provided according to an embodiment of the disclosure.

An embodiment of the disclosure provides an airway anomaly recognition apparatus. FIG. 7 is a schematic structural diagram of the airway anomaly recognition apparatus provided according to an embodiment of the disclosure. As shown in FIG. 7, the apparatus includes:

an acquisition module 701 for acquiring a ventilation parameter, the ventilation parameter includes at least one of an airway pressure and an airway flow;

a recognition module 702 for recognizing, according to a change of the ventilation parameter, whether an airway anomaly event occurs; and an output module 703 for outputting an airway anomaly event prompt when it is recognized that the airway anomaly event occurs.

Optionally, the airway anomaly event includes one or more of a water accumulation in circuit, a sputum accumulation and a circuit resistance increase.

Optionally, the step of recognizing, by the recognition module 702 according to a change of the ventilation parameter, whether an airway anomaly event occurs includes:

determining, when the ventilation parameter continuously jitters, that a water accumulation in circuit occurs.

Optionally, the step of recognizing, by the recognition module 702 according to a change of the ventilation parameter, whether an airway anomaly event occurs includes:

performing a spectral analysis on the ventilation parameter; and determining, if a high-frequency component of the ventilation parameter is greater than a preset first threshold, that a water accumulation in circuit occurs.

Optionally, the step of recognizing, by the recognition module 702 according to a change of the ventilation parameter, whether an airway anomaly event occurs includes:

performing curve fitting on the ventilation parameter;

calculating an error between the fitted curve and the ventilation parameter; and determining, if the error is greater than a preset second threshold, that a water accumulation in circuit occurs.

Optionally, the step of recognizing, by the recognition module 702 according to a change of the ventilation parameter, whether an airway anomaly event occurs includes:

calculating an airway resistance through the airway pressure and the airway flow; and if the airway resistance increases, determining that a sputum accumulation occurs.

Optionally, the airway pressure includes an inspiratory pressure and an expiratory pressure, and the step of recognizing, by the recognition module 702 according to a change of the ventilation parameter, whether an airway anomaly event occurs includes:

determining, through the inspiratory pressure and the expiratory pressure, whether a circuit resistance increase occurs.

Optionally, the step of determining, by the recognition module 702 through the inspiratory pressure and the expiratory pressure, whether a circuit resistance increase occurs includes:

calculating a current pipeline pressure drop through the inspiratory pressure and the expiratory pressure; and determining, if a difference between the current pipeline pressure drop and an initial pipeline pressure drop is greater than a preset third threshold, that a circuit resistance increase occurs.

Optionally, the step of determining, by the recognition module 702 through the inspiratory pressure and the expiratory pressure, whether a circuit resistance increase occurs includes:

calculating a change in pressure drop of the pipeline through the inspiratory pressure and the expiratory pressure; and determining, if an increase value in pressure drop of the pipeline is greater than a preset fourth threshold, that a circuit resistance increase occurs.

Optionally, the airway flow includes an inspiratory flow and an expiratory flow, the inspiratory pressure is calculated through the inspiratory flow, and the expiratory pressure is calculated through the expiratory flow.

An embodiment of the disclosure provides an airway anomaly recognition apparatus, which acquires a ventilation parameter, the ventilation parameter includes at least one of an airway pressure and an airway flow; recognizes, according to a change of the ventilation parameter, whether an airway anomaly event occurs; and outputs an airway anomaly event prompt when it is recognized that the airway anomaly event occurs. That is to say, the airway anomaly recognition apparatus provided according to one embodiment of the disclosure may recognize a specific airway anomaly event and make a prompt according to a change of the ventilation parameter, which facilitates the handling of the airway anomaly event by an operator and ensures the normal ventilation of the ventilation device, thereby improving the treatment effect.

Figure 8:
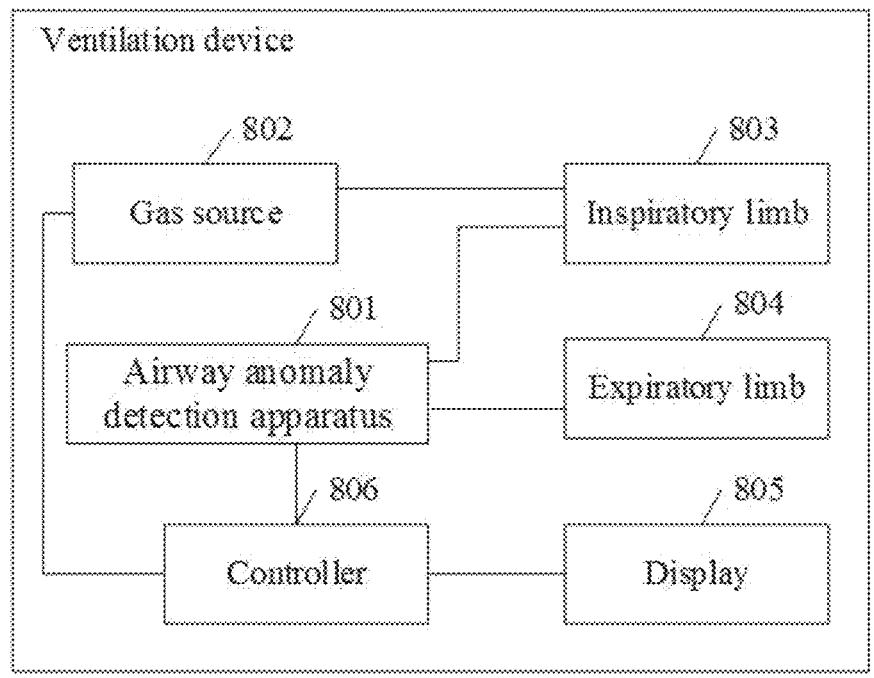
FIG. 8 is a first schematic structural diagram I of the ventilation device provided according to an embodiment of the disclosure.

An embodiment of the disclosure provides a ventilation device. FIG. 8 is a first schematic structural diagram I of ventilation recognition provided according to an embodiment of the disclosure. As shown in FIG. 8, the ventilation device includes: the above airway anomaly recognition apparatus 801, and further includes a gas source 802, an inspiratory limb 803, an expiratory limb 804, a display 805, and a controller 806;

the gas source 802 provides a gas during mechanical ventilation;

the inspiratory limb 803 is connected to the gas source 802 and provides an inspiratory path during the mechanical ventilation;

the expiratory limb 804 provides an expiratory path during the mechanical ventilation;

the airway anomaly recognition apparatus 801 is connected to the inspiratory limb 803, the expiratory limb 804 and the controller 806;

the airway anomaly recognition apparatus 801 recognizes an airway anomaly event during the mechanical ventilation;

the controller 806 is further connected to the gas source 802 and controls the process of the mechanical ventilation; and the display 805 is connected to the controller 806 and displays a respiratory waveform during the mechanical ventilation.

Figure 9:
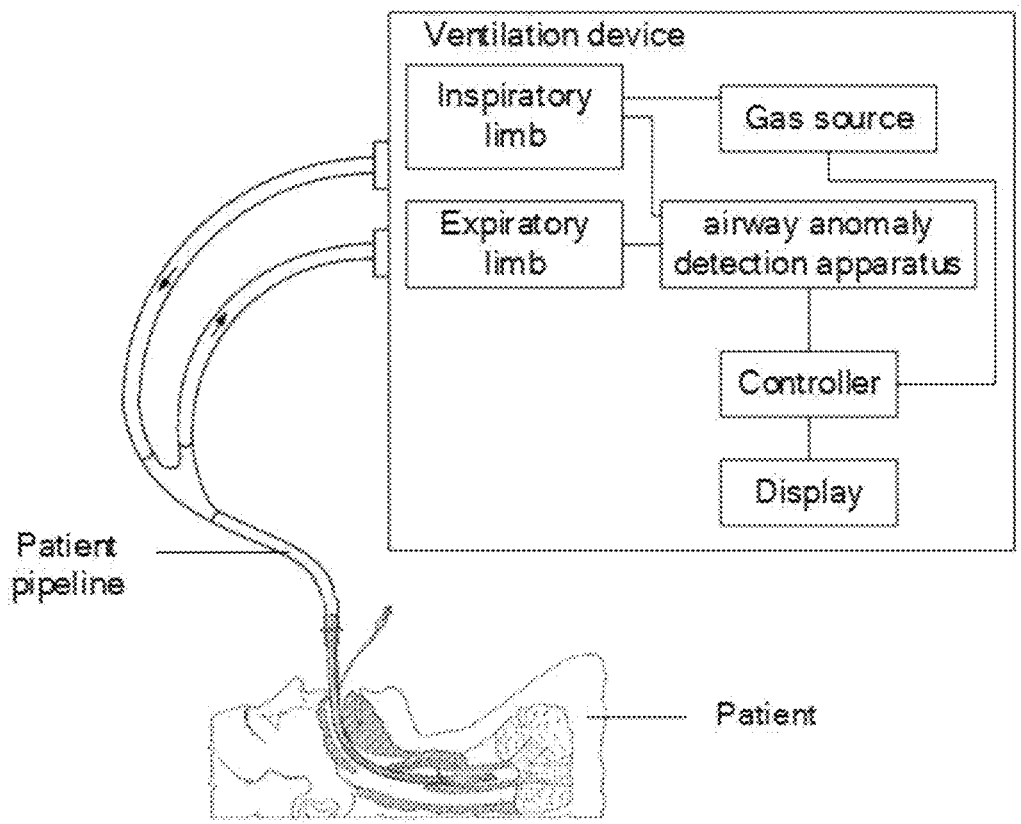
FIG. 9 is a second schematic structural diagram II of the ventilation device provided according to an embodiment of the disclosure.

FIG. 9 is a second schematic structural diagram II of the ventilation device provided according to an embodiment of the disclosure. As shown in FIG. 9, a patient may be connected to the ventilation device through a patient pipeline to implement the mechanical ventilation, the ventilation device includes the above airway anomaly recognition apparatus.

An embodiment of the disclosure provides a computer-readable storage medium, the computer-readable storage medium stores an airway anomaly recognition program, and the airway anomaly recognition program is executable by a processor to implement the above airway anomaly recognition method. The computer-readable storage medium may be a volatile memory, such as a Random-Access Memory (RAM), or a non-volatile memory, such as a Read-Only Memory (ROM), a flash memory, a Hard Disk Drive (HDD) or a Solid-State Drive (SSD); or a respective device including one or any combination of the above memories, such as a mobile phone, a computer, a tablet, and a personal digital assistant.

Those skilled in the art should understand that the embodiments of the disclosure may be provided as a method, a system, or a computer program product. Therefore, the disclosure may take the form of hardware embodiments, software embodiments, or embodiments with a combination of software and hardware. Moreover, the disclosure may take the form of a computer program product that is implemented on one or more computer-usable storage media (including but not limited to a disk memory and an optical memory, etc.) that include computer-usable program codes.

The disclosure is described with reference to flow charts and/or block diagrams of the methods, devices (systems), and computer program products according to the embodiments of the disclosure. It should be understood that each procedure and/or block in the flow charts and/or block diagrams, and combinations of the procedures and/or blocks in the flow charts and/or block diagrams may be implemented by computer program instructions. These computer program instructions may be provided to a processor of a general-purpose computer, a special-purpose computer, an embedded processor or other programmable signal processing devices to create a machine, such that the instructions executed by the processor of the computer or other programmable signal processing devices create an apparatus for implementing functions specified in one or more procedures in the flow charts and/or one or more blocks in the block diagrams.

These computer program instructions may also be stored in a computer-readable memory that may direct the computer or other programmable signal processing device to operate in a specific manner, such that the instructions stored in the computer-readable memory create an article of manufacture including an instruction apparatus, and the instruction apparatus implements the functions specified in one or more procedures of the flow charts and/or one or more blocks of the block diagrams.

These computer program instructions may also be loaded onto the computer or other programmable signal processing devices, such that a series of operation steps are executed on the computer or other programmable devices to perform computer-implemented processing, and thus the instructions executed on the computer or other programmable devices provide steps for implementing the functions specified in one or more procedures of the flow charts and/or one or more blocks of the block diagrams.

The above description is only some embodiments of the disclosure, and is not intended to limit the scope of protection of the disclosure.

INDUSTRIAL APPLICABILITY

In the technical solution of the embodiments of the disclosure, the airway anomaly recognition apparatus acquires a ventilation parameter, the ventilation parameter includes at least one of an airway pressure and an airway flow; recognizes, according to a change of the ventilation parameter, whether an airway anomaly event occurs; and outputs an airway anomaly event prompt when it is recognized that the airway anomaly event occurs. That is to say, in the technical solution provided according to the embodiments of the disclosure, according to a change of the ventilation parameter, a specific airway anomaly event may be recognized and a prompt is made, which facilitates the handling of the airway anomaly event by an operator and ensures the normal ventilation of the ventilation device, thereby improving the treatment effect.

What is claimed is:

1. An airway anomaly detection method for a ventilation device, comprising:
  acquiring, by at least one flow sensor provided in an inspiratory limb or an expiratory limb of the ventilation device, a ventilation parameter, wherein the ventilation parameter comprises at least one of an airway pressure and an airway flow;
  determining, by the ventilation device and according to a change of the ventilation parameter, whether an airway anomaly event occurs; and
  outputting, from the ventilation device, an airway anomaly event prompt when it is determined that the airway anomaly event occurs, wherein
  the airway anomaly event comprises a water accumulation, and determining whether the airway anomaly event occurs comprises:
    performing a spectral analysis on the ventilation parameter to determine a frequency that is greater than a preset frequency threshold and determine a high-frequency component of the ventilation parameter at the determined frequency; and
    determining, if the high-frequency component of the ventilation parameter is greater than a preset first threshold, that the water accumulation in circuit occurs,
  wherein the airway anomaly event prompt causes a medical care personnel to perform an operation on the ventilation device.

2. The airway anomaly detection method of claim 1, wherein the airway anomaly event further comprises one or more of a sputum accumulation and a circuit resistance increase.

3. The airway anomaly detection method of claim 1, wherein determining whether the airway anomaly event occurs further comprises:
  determining, when the ventilation parameter continuously jitters, that the water accumulation in circuit occurs.

4. The airway anomaly detection method of claim 1, wherein determining whether the airway anomaly event occurs further comprises:
  performing curve fitting on the ventilation parameter:
  calculating an error between the fitted curve and the ventilation parameter; and
  determining, if the error is greater than a preset second threshold, that the water accumulation in circuit occurs.

5. The airway anomaly detection method of claim 2, wherein determining whether the airway anomaly event occurs further comprises:
  calculating an airway resistance based on the airway pressure and the airway flow; and
  determining, if the airway resistance increases, that the sputum accumulation occurs.

6. The airway anomaly detection method of claim 2, wherein the airway pressure comprises an inspiratory pressure and an expiratory pressure, and determining whether the airway anomaly event occurs further comprises:
  determining, based on the inspiratory pressure and the expiratory pressure, whether the circuit resistance increase occurs.

7. The airway anomaly detection method of claim 6, wherein determining, based on the inspiratory pressure and the expiratory pressure, whether the circuit resistance increase occurs comprises:
  calculating a current pipeline pressure drop based on the inspiratory pressure and the expiratory pressure; and
  determining, if a difference between the current pipeline pressure drop and an initial pipeline pressure drop is greater than a preset third threshold, that the circuit resistance increase occurs.

8. The airway anomaly detection method of claim 6, wherein determining, based on the inspiratory pressure and the expiratory pressure, whether the circuit resistance increase occurs comprises:
  calculating a change in pressure drop of a pipeline based on the inspiratory pressure and the expiratory pressure; and
  determining, if an increase value in pressure drop of the pipeline is greater than a preset fourth threshold, that the circuit resistance increase occurs.

9. The airway anomaly detection method of claim 6, wherein the airway flow comprises an inspiratory flow and an expiratory flow, the inspiratory pressure is calculated based on the inspiratory flow, and the expiratory pressure is calculated based on the expiratory flow.

10. A ventilation device, comprising an airway anomaly detection apparatus, a gas source, an inspiratory limb, an expiratory limb, a display, at least one flow sensor, and a controller; wherein
  the gas source provides a gas during mechanical ventilation;
  the inspiratory limb is connected to the gas source and provides an inspiratory path during the mechanical ventilation;
  the expiratory limb provides an expiratory path during the mechanical ventilation;
  the controller is connected to the gas source and controls a process of the mechanical ventilation;
  the flow sensor is provided in the inspiratory limb or the expiratory limb, and the flow sensor is configured to measure at least one of an airway pressure and an airway flow during the process of the mechanical ventilation;
  the display is connected to the controller and displays a respiratory waveform during the process of the mechanical ventilation; and
  the airway anomaly detection apparatus is connected to the inspiratory limb, the expiratory limb and the controller, and the airway anomaly detection apparatus is configured to detect an airway anomaly event during the mechanical ventilation, wherein the airway anomaly detection apparatus is specifically configured to:
  acquire a ventilation parameter, comprising at least one of the airway pressure and the airway flow, measured by the flow sensor;
  determine, according to a change of the ventilation parameter, whether the airway anomaly event occurs; and
  output an airway anomaly event prompt when it is determined that the airway anomaly event occurs; wherein the airway anomaly event comprises a water accumulation, and the airway anomaly detection apparatus is further configured to:
  perform a spectral analysis on the ventilation parameter to determine a frequency that is greater than a preset frequency threshold and determine a high-frequency component of the ventilation parameter at the determined frequency; and
  determine, if the high-frequency component of the ventilation parameter is greater than a preset first threshold, that the water accumulation in circuit occurs,
  wherein the airway anomaly event prompt causes a medical care personnel to perform an operation on the ventilation device.

11. The ventilation device of claim 10, wherein the airway anomaly event further comprises one or more of a sputum accumulation and a circuit resistance increase.

12. The ventilation device of claim 10, wherein to determine whether the airway anomaly event occurs, the airway anomaly detection apparatus is further configured to:
  determine, when the ventilation parameter continuously jitters, that the water accumulation in circuit occurs.

13. The ventilation device of claim 10, wherein to determine whether the airway anomaly event occurs, the airway anomaly detection apparatus is further configured to:
  perform curve fitting on the ventilation parameter:
  calculate an error between the fitted curve and the ventilation parameter; and
  determine, if the error is greater than a preset second threshold, that the water accumulation in circuit occurs.

14. The ventilation device of claim 11, wherein to determine whether the airway anomaly event occurs, the airway anomaly detection apparatus is further configured to:
  calculate an airway resistance based on the airway pressure and the airway flow; and
  determine, if the airway resistance increases, that the sputum accumulation occurs.

15. The ventilation device of claim 11, wherein the airway pressure comprises an inspiratory pressure and an expiratory pressure, and to determine whether the airway anomaly event occurs, the airway anomaly detection apparatus is further configured to:
  determine, based on the inspiratory pressure and the expiratory pressure, whether the circuit resistance increase occurs.

16. The ventilation device of claim 15, wherein to determine, based on the inspiratory pressure and the expiratory pressure, whether the circuit resistance increase occurs, the airway anomaly detection apparatus is further configured to:
  calculate a current pipeline pressure drop based on the inspiratory pressure and the expiratory pressure; and
  determine, if a difference between the current pipeline pressure drop and an initial pipeline pressure drop is greater than a preset third threshold, that the circuit resistance increase occurs.

17. The ventilation device of claim 15, wherein to determine, based on the inspiratory pressure and the expiratory pressure, whether the circuit resistance increase occurs, the airway anomaly detection apparatus is further configured to:
  calculate a change in pressure drop of a pipeline based on the inspiratory pressure and the expiratory pressure; and
  determine, if an increase value in pressure drop of the pipeline is greater than a preset fourth threshold, that the circuit resistance increase occurs.

18. A ventilation device, comprising an airway anomaly detection apparatus, a gas source, an inspiratory limb, an expiratory limb, a display, at least one flow sensor, and a controller; wherein
  the gas source provides a gas during mechanical ventilation;

the inspiratory limb is connected to the gas source and provides an inspiratory path during the mechanical ventilation;

the expiratory limb provides an expiratory path during the mechanical ventilation;

the controller is connected to the gas source and controls a process of the mechanical ventilation;

the flow sensor is provided in the inspiratory limb or the expiratory limb, and the flow sensor is configured to measure at least one of an airway pressure and an airway flow during the process of the mechanical ventilation;

the display is connected to the controller and displays a respiratory waveform during the process of the mechanical ventilation; and the airway anomaly detection apparatus is connected to the inspiratory limb, the expiratory limb and the controller, and the airway anomaly detection apparatus is configured to detect an airway anomaly event during the mechanical ventilation, wherein the airway anomaly detection apparatus is specifically configured to:

acquire a ventilation parameter, comprising at least one of the airway pressure and the airway flow, measured by the flow sensor;

determine, according to a change of the ventilation parameter, whether the airway anomaly event occurs; and output an airway anomaly event prompt when it is determined that the airway anomaly event occurs;

wherein the airway anomaly event comprises a water accumulation, and the airway anomaly detection apparatus is further configured to:

perform curve fitting on the ventilation parameter;

calculate an error between the fitted curve and the ventilation parameter, and determine, if the error is greater than a preset second threshold, that the water accumulation in circuit occurs, wherein the airway anomaly event prompt causes a medical care personnel to perform an operation on the ventilation device.

* * * * *